US007528166B2

(12) United States Patent
Eklund et al.

(10) Patent No.: US 7,528,166 B2
(45) Date of Patent: May 5, 2009

(54) LIGNAN DERIVATIVES

(75) Inventors: Patrik Eklund, Turku (FI); Mervi Hiilovaara-Teijo, Riihikoski (FI); Arja Kalapudas, Oulu (FI); Lauri Kangas, Lieto (FI); Anna Lindholm, Bandhagen (SE); Rainer Sjohölm, Piispanristi (FI); Marja Södervall, Oulu (FI); Mikko Unkila, Littoinen (FI)

(73) Assignee: Hormos Medical Corporation, Turku (FI)

( * ) Notice: Subject to any disclaimer, the term of this patent is extended or adjusted under 35 U.S.C. 154(b) by 599 days.

(21) Appl. No.: 10/499,452

(22) PCT Filed: Jan. 21, 2003

(86) PCT No.: PCT/FI03/00041

§ 371 (c)(1),
(2), (4) Date: Jun. 18, 2004

(87) PCT Pub. No.: WO03/066556

PCT Pub. Date: Aug. 14, 2003

(65) Prior Publication Data

US 2005/0101541 A1    May 12, 2005

(30) Foreign Application Priority Data

Feb. 5, 2002    (FI)    ................................. 20020222
Mar. 25, 2002    (FI)    ................................. 20020563

(51) Int. Cl.
  *A61K 31/341*    (2006.01)
(52) U.S. Cl. ...................................... 514/461; 549/323
(58) Field of Classification Search ................. 568/660; 549/358, 432, 448, 456, 157, 323; 562/76, 562/100, 103; 514/461
See application file for complete search history.

(56) References Cited

U.S. PATENT DOCUMENTS

| 4,103,006 | A | * | 7/1978 | Sih ............................. 514/25 |
| 4,343,796 | A | * | 8/1982 | Groen .......................... 514/63 |
| 4,708,820 | A | * | 11/1987 | Namiki et al. ............... 252/398 |
| 4,808,574 | A | * | 2/1989 | Brekhman et al. ............ 514/23 |
| 4,816,481 | A | * | 3/1989 | Takasugi et al. ............. 514/470 |
| 4,889,927 | A | * | 12/1989 | Murakami et al. ......... 536/18.6 |
| 5,702,752 | A | * | 12/1997 | Gugger et al. ............... 426/634 |
| 5,827,898 | A | | 10/1998 | Khandwala et al. ......... 514/734 |
| 5,837,256 | A | * | 11/1998 | Clark et al. .................. 514/25 |
| 5,853,731 | A | | 12/1998 | Wu et al. ................... 424/195.1 |
| 6,063,383 | A | * | 5/2000 | Hsu et al. ................... 424/764 |
| 6,210,942 | B1 | * | 4/2001 | Lewis et al. ................. 435/183 |
| 6,261,565 | B1 | * | 7/2001 | Empie et al. ................ 424/757 |
| 6,271,257 | B1 | * | 8/2001 | Mutanen ..................... 514/461 |
| 6,284,789 | B1 | * | 9/2001 | LaLonde et al. ............. 514/451 |
| 6,451,849 | B1 | * | 9/2002 | Ahotupa et al. ............. 514/473 |
| 6,486,126 | B1 | * | 11/2002 | Prasad ......................... 514/25 |
| 6,635,459 | B1 | * | 10/2003 | Lewis et al. ................. 435/190 |
| 6,689,809 | B2 | * | 2/2004 | Ahotupa et al. ............. 514/473 |
| 7,097,862 | B2 | * | 8/2006 | Hodge ......................... 424/725 |
| 2001/0016590 | A1 | | 8/2001 | Ahotupa et al. ............. 514/310 |

FOREIGN PATENT DOCUMENTS

| EP | 0 038 600 | 10/1981 |
| EP | 0 043 150 | 1/1982 |
| WO | WO 88/03800 | 6/1988 |
| WO | WO 97/14670 | 4/1997 |

OTHER PUBLICATIONS

Ichikawa et al. "The calcium antagonist . . . " CA 106:43444 (1987).*
Umehara et al. "Studies on differentiation . . . " CA 126:139494 (1997).*
Shin et al. "Lignan from calyces . . . " CA 103:19834 (1985).*
Bundgaard et al. "prodrugs . . . " Ca 105:102424 (1986).*
Lokind et al. "Oral bioavaila . . . " CA 124:270254 (1996).*
Potter et al. "Hydroxylation- . . . " CA 131:175072 (1999).*
Exhibit I*
Nudelman et al. "Novel mutal prodrug . . . " Mde. Chem. 43, p. 2962-2966 (2000).*
Bundgaard "Prodrug design" p. 1-3 (1986).*
Umehara et al. "Studies on differentiation inducers . . . " CA 126:139494 (1997).*
Umehara et al. "Studies on differrentiation . . . " Chem. Pharm. bull. 44(2)2300-2304 (1996).*
Drake et al., "D, Naturstoffe: Hormone*), Vitamine**) and Naturstoffe," *Chem Zentralblall II* 2963 (1935).
Haworth et al., "The Constituents of Natural Phenolic Resins. Part XVII, A Synthesis of 1-Matairesinol," *J. Chem. Soc.* 1098-1101 (1940).
Wu et al., "Bioactive Constitutents from the Stems of Annona Montana," 61 *Planta Med*. 146-149 (1995).
Chao et al., "Novel Action of Lignans Isolated from Hernandia Nymphaeifolia on $Ca^{2+}$Signaling in Renal Tubular Cells," 443 *European Journal of Pharmacology* 31-38 (2002).
Araújo et al., "Protective Effects of Yangambin on Cardiovascular Hyporeactivity to Catecholamines in Rats with Endotoxin-induced Shock," 363 *Naunyn-Schmiedeberg's Arch Pharmacol* 267-275 (2001).
Oka et al., "Antitumor Agents Containing Arctigenin or Matairesinol Derivatives," 111:102693 *Caplus* (1989).

(Continued)

*Primary Examiner*—Celia Chang
(74) *Attorney, Agent, or Firm*—James C. Lydon

(57) ABSTRACT

Novel phenolic esters of lignans, and pharmaceutical compositions, dietary supplements, and food products containing these esters.

2 Claims, No Drawings

OTHER PUBLICATIONS

Yoda et al., "Novel Stereoselective Synthesis of (-)-Enterolactone Employing Chiral Unsaturated Lactam," 48 *Tetrahedron* 3313-3322 (1992).

Serra et al., "Anti-Allergic Properties of the Natural PAF Antagonist Yangambin," 63 *Planta Medica* 207-212 (1997).

Umehara et al., " Studies on Differentiation Inducers. VI.[1)] Lignan Derivatives from Arctium Fructus. (2)," 44 *Chem. Pharm. Bull.* 2300-2304 (1996).

Cristiano et al., "Metal Assisted Reactions. Part 25. Heterogeneous and Homogeneous Catalytic Transfer Hydrogenolysis of Allyloxytetrazoles to yield Alkenes or Alkanes," 125:142643 *American Chemical Society* (1997).

Ahn et al., "Inhibitory Activity of Lignan Components from the Flower Buds of Magnoliae Fargesii on the Expression of Cell Adhesion Molecules," 24 *Biol. Pharm. Bull.* 1085-1087 (2001).

Ikegawa et al., "Extraction of Anticancer and Antiviral Substances from Stellera Chamaejasme for Therapeutic Use," 125:41748 *Caplus* (1996).

Oka et al., "Lignans as Antitumor Agents," 112:216455 *Caplus* (1990).

Oka et al., "Preparation of Dibenzylbutanediol and Dibenzyltetrahydrofuran Derivatives as Immunosuppressants," 114:23554 *Caplus* (1991).

Rajagopal et al., "Palladium-catalyzed Transfer Hydrogenolysis of Benzyl Acetate with Ammonium Formate," 126:305344 *American Chemical Society* (1998).

Hu et al., "Removal of Phenolic Hydroxyl Groups in Lignin Model Compounds and its Effect on Photostability," 133:90884 *American Chemical Society* (2000).

* cited by examiner

LIGNAN DERIVATIVES

This application is a U.S. National Stage of International application PCT/FI03/00041, filed Jan. 21, 2003.

FIELD OF THE INVENTION

This invention relates to novel phenolic esters, particularly phenolic diesters of lignans. Furthermore, the invention concerns pharmaceutical compositions, dietary supplements, and food products comprising said esters.

BACKGROUND OF THE INVENTION

The publications and other materials used herein to illuminate the background of the invention, and in particular, cases to provide additional details respecting the practice, are incorporated by reference.

Lignans are phenolic compounds widely distributed in plants. They can be found in different parts (roots, leafs, stem, seeds, fruits) but mainly in small amounts. In many sources (seeds, fruits), lignans are found as glycosidic conjugates associated with fiber component of plants. The most common dietary sources of mammalian lignan precursors are unrefined grain products. The highest concentrations in edible plants have been found in flaxseed, followed by unrefined grain products, particularly rye.

Considerable amounts of lignans are also found in coniferous trees. The type of lignans differs in different species and the amounts of lignans vary in different parts of the trees. The typical lignans in heart wood of spruce (*Picea abies*) are hydroxymatairesinol (HMR), α-conidendrin, conidendrinic acid, matairesinol, isolariciresinol, secoisolariciresinol, liovile, picearesinol, lariciresinol and pinoresinol (Ekman 1979). The far most abundant single component of lignans in spruce is HMR, about 60 percent of total lignans, which occurs mainly in unconjugated free form.

Plant lignans such as hydroxymatairesinol, matairesinol and secoisolariciresinol, are converted by gut microflora to mammalian lignans, enterolactone or enterodiol (Axelson et al., 1982; WO 00/59946). A recent study (Heinonen et al., 2001) shows also that matairesinol, secoisolariciresinol, lariciresinol and pinoresinol glucoside were to be converted to enterolactone.

Lignans have putative beneficial effects on human health. The health benefits obtained with lignan rich diet include (Adlercreutz 1998; Vanharanta et al. 2002):

1) decreased breast cancer risk
2) decreased risk of prostate cancer risk
3) decreased risk for cardiovascular disease risk Based on studies on their biological activities, lignans may also suppress immunological overactivity and thus be of use in preventing a immunological disease.

According to our experience, lignans (hydroxymatairesinol, matairesinol and enterolactone) are well absorbed molecules from the gastrointestinal tract. However, as can be seen from Scheme 1 disclosing the structure of certain lignans, the lignans contain hydroxyl groups, and such hydroxyl groups are targets of phase II metabolic reactions (conjugation into glucuronic acid, sulfonate or glutathione conjugates). Especially phenolic hydroxyl groups are likely targets for these reactions.

It is known that metabolites after phase II conjugation reactions are almost invariably pharmacologically inactive. The inactivity results from the inability of conjugated metabolites to penetrate cell membranes and thus be disposited into tissues, but they are rather being rapidly eliminated into the urine (by way of kidneys) or into the intestine (by way of hepatobiliary excretion).

Thus, conjugation is considered as an inactivation process of various molecules, including lignans.

SUMMARY OF THE INVENTION

The aim of this invention is to protect the phase II conjugation reactive phenolic hydroxy groups and optionally also other hydroxy groups of lignans by converting the same to ester groups. The benefit of such modification is protracted rate of phase II conjugation reactions, and thus better bioavailability of the administered lignan ester.

According to one aspect, this invention concerns a compound of formula (I)

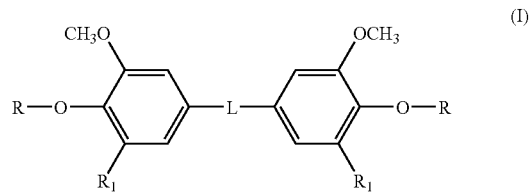

or formula (II)

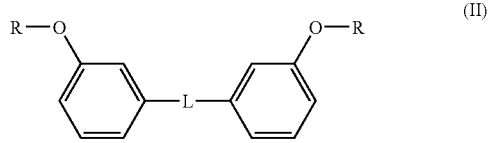

wherein L is a lignan skeleton, which optionally includes a bridge forming a ring with one of the phenyl groups in the formulae, and L in compound (I) is a lignan skeleton of any of the lignans hydroxymatairesinol, matairesinol, lariciresinol, secoisolariciresinol, isolariciresinol, oxomatairesinol, alpha-conidendrin, pinoresinol, liovil, picearesinol, arctigenin, syringaresinol or nortrachelogenin; $R_1$ is H or methoxy, and R is methyl, R'—CO— or R'—$SO_2$—, wherein R' is a $C_1$ to $C_{22}$ alkyl, alkenyl, arylalkyl, aralkenyl, or an aromatic group, and R' is unsubstituted or substituted with one or more hydroxy groups and/or one or more carboxyl groups, an oxo group or an amino group, or a geometric isomer or a stereoisomer thereof, provided that R is methyl only in a single R—O— substituent in a compound of formula (I) where L is a skeleton of the lignan arctigenin, and R is not acetyl, benzoyl, 4-hydroxybenzoyl, 4-nitrobenzoyl or 3-methoxy-4-hydroxybenzoyl, and R is not propionyl in the compound of formula (II) if L is the skeleton of enterodiol.

According to another aspect, this invention concerns a pharmaceutical composition or a dietary supplement composition comprising an active ingredient a compound of formula (I)

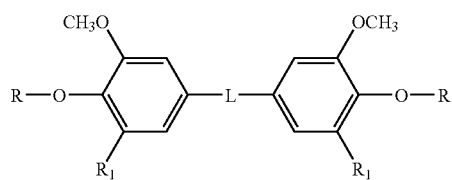

or formula (II)

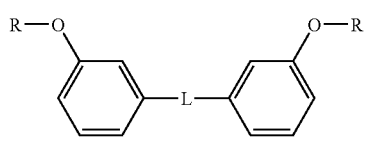

wherein L is a lignan skeleton, which optionally includes a bridge forming a ring with one of the phenyl groups in the formulae, and L in compound (I) is a lignan skeleton of any of the lignans hydroxymatairesinol, matairesinol, lariciresinol, secoisolariciresinol, isolariciresinol, oxomatairesinol, alpha-conidendrin, pinoresinol, liovil, picearesinol, arctigenin, syringaresinol or nortrachelogenin; $R_1$ is H or methoxy, and R is methyl, R'—CO— or R'—$SO_2$—, wherein R' is a $C_1$ to $C_{22}$ alkyl, alkenyl, arylalkyl, aralkenyl, or an aromatic group, and R' is unsubstituted or substituted with one or more hydroxy groups and/or one or more carboxyl groups, an oxo group or an amino group, or a geometric isomer or a stereoisomer thereof, provided that R is methyl only in a single R—O— substituent in a compound of formula (I) where L is a skeleton of the lignan arctigenin, and R is not acetyl or propionyl in a compound of formula (II) where L is the lignan skeleton of enterodiol, and an acceptable carrier.

According to a third aspect, this invention concerns a food product, especially a functional food, a nutritional supplement, a nutrient, a pharmafood, a nutraceutical, a health food, a clinical nutrition product, a designer food or any food product, comprising an active ingredient a compound of formula (I)

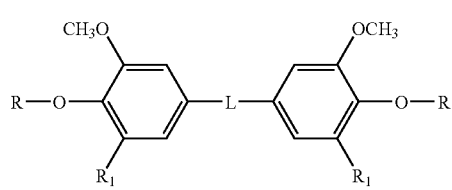

or formula (II)

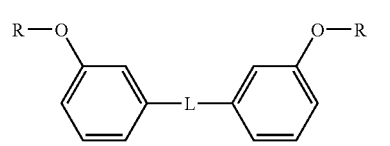

wherein L is a lignan skeleton, which optionally includes a bridge forming a ring with one of the phenyl groups in the formulae, and L in compound (I) is a lignan skeleton of any of the lignans hydroxymatairesinol, matairesinol, lariciresinol, secoisolariciresinol, isolariciresinol, oxomatairesinol, alpha-conidendrin, pinoresinol, liovil, picearesinol, arctigenin, syringaresinol or nortrachelogenin; $R_1$ is H or methoxy, and R is methyl, R'—CO— or R'—$SO_2$—, wherein R' is a $C_1$ to $C_{22}$ alkyl, alkenyl, arylalkyl, aralkenyl, or an aromatic group, and R' is unsubstituted or substituted with one or more hydroxy groups and/or one or more carboxyl groups, an oxo group or an amino group, or a geometric isomer or a stereoisomer thereof, provided that R is methyl only in a single R—O— substituent in a compound of formula (I) where L is a skeleton of the lignan arctigenin, and a foodstuff.

DETAILED DESCRIPTION OF THE INVENTION

The metabolic phase II conjugation-reactive groups in drugs or nutraceutical ingredients, often hydroxyl, may be modified, or masked by chemically linking other molecules onto these residues. Esterification of hydroxyl groups with carboxylic fatty acids, or sulfonic acids, is common practice for those skilled in the art. The resulting molecule from such modification can be mono-, di- or higher ester, depending how many hydroxyl groups were modified of a given molecule.

After being absorbed, the esteric bonds may be cleaved off by specific enzymatic reactions catalysed by a group of enzymes called esterases. Such reactions may take place within bloodstream, or within a tissue expressing a suitable amount of the needed enzyme. After cleavage of the ester bond, the hydroxyl group is re-established, and the parent molecule (in this case the lignan) is reconstituted. In pharmaceutical development, the molecule which behaves in the manner described above, is be called a pro-drug, which, after entering the systemic circulation and/or tissues, is being converted into metabolically active molecule which can be excreted. The importance of this phenomenon is the avoidance of the liver first-pass metabolism (a metabolic process of drugs during the absorption phase from the gastro-intestinal tract) which often dramatically decreases the relative amount of biologically active, bioavailable pool of the administered drug. An exemplar of this process is a common anti-inflammatory drug salisylic acid, which is extensively metabolised into conjugates, resulting in poor bioavailability. However, derivatization of the salisylic acid into an ester, for example acetylsalisylic acid, dramatically inhibits the first-pass metabolism and elevates the bioavailable portion of the absorbed drug and enhances the pharmacodynamic effect.

As can be seen in Scheme 1, lignans bear typically two phenyl substituents, which in turn are substituted with at least a hydroxy group. The lignan skeleton L in the formulae (I) and (II) stands for the part of the lignan molecule bearing such phenyl substituents. As further can be seen, many of the lignans have also one or more hydroxy groups in the skeleton L.

Based on the above considerations, the following benefits may be expected after esterification of the phenolic hydroxy groups, optionally in combination with esterification of part or all of the hydroxy groups in the lignan skeleton:

1) Enhanced bioavailability because of inhibited first-pass metabolism (phase II conjugation reactions) of the lignan
2) Because of 1, higher tissue levels of the lignan, and thus organ specific effects (antioxidative, tumor inhibition, brain antioxidant) are possible
3) Simultaneous delivery of the carrier, which may also have independent beneficial health effects, depending on the linked molecule Preferred plant lignans for the purpose of this invention are, for example, hydroxymatairesinol, matairesinol, lariciresinol, secoisolariciresinol, isolariciresinol, oxomatairesinol, alpha-conidendrin, pinoresinol, liovil, picearesinol, nortrachelogenin, arctigenin, syringaresinol, enterolactone or enterodiol and their geometric isomers and stereoisomers.

Particularly preferred plant lignans are hydroxymatairesinol, matairesinol, lariciresinol, secoisolariciresinol and isolariciresinol and their geometric isomers and stereoisomers.

Preferred mammalian lignans are enterolactone and enterodiol, especially enterolactone.

Preferable acids for the esterification are, for example, mono- or dicarboxylic fatty acids, hydroxy acids and sulfonic acids. As examples of suitable dicarboxylic acids can be mentioned succinic acid, glutaric acid and malonic acid. Lactic acid is an example of hydroxysubstituted acids. Tartaric acid and citric acid are examples of acids with several carboxylic groups and one or more hydroxy groups.

A particularly preferable acid is butyric acid, which is normally present in human large intestine. Butyrates are a metabolic fermentation products produced by the intestinal bacteria using complex carbohydrates (starches, non-starch polysaccharides) as their energy sources. In fact, the intestinal epithelial cells of the host may use the produced butyrates as their energy source.

Butyrates have been shown to have anti-cancer properties. They inhibits proliferation of cancerous cells of several types (Heerdt et al., 1999; McBain et al., 1997; Bordonaro et al., 1999). Furthermore, butyric acid exhibit chemopreventive activity in e.g. animal models of mammary (Belobrajdic and McIntosh, 2000) and colon cancers (Avivi-Green et al., 2000; Gostner et al., 2000). In addition, butyrates have been implicated with anti-inflammatory properties (Säemann et al., 2000) and other conditions such as spinal muscular atrophy (Chang et al., 2001). Thus, dietary or pharmacological treatments to enhance butyrate formation or levels in target organs may lead to therapeutic or chemopreventive endpoints in various disease.

Butyric acid derivatives have also been proposed as a prodrugs for pharmaceutical anti-cancer drugs. For example, butyrate esters of campothecin and 9-nitrocamphotecin, antitumor compounds, were effective while many other aliphatic esters were inactive (Han et al., 1999). Likewise, a prodrug butyric acid ester of all-trans-retinoic acid was shown to be more effective than the parent molecule (Nudelman and Rephaeli, 2000).

Thus, we believe that lignane butyrates may enhance a chemopreventive effect, compared to the lignan effect only. This is due to the fact, that the ester bonds are cleaved, resulting in liberation of butyric acid off the lignan, butyric acid may bring about the chemopreventive effects of its own. Butyrate prodrug of lignan thus serves as depot release of two active ingredients that may act through different mechanisms.

As the last aspect, the butyric acid prodrug may enhance the bioavailability by two mechanisms. First, the lipid membrane permeability of lignan may be enhanced because the hydrophilic hydroxyl residues of lignan are masked with lipophilic butyrate molecules. This may result in enhanced absorption from the gastro-intestinal tract, as well as enhanced distribution into tissues which are otherwise difficult to be able to reach (such as brain due to blood brain barrier). The second mechanism by which a butyrate prodrug of lignan can enhance the bioavailability relates to the above-described inhibition of liver first pass phase II conjugation reactions.

Certain phenolic esters of lignans are known from the literature, namely the dibenzoate and the p-nitrodibenzoate of matairesinol; enterolactone diacetate; monoacetate, triacetate, p-hydroxymonobenzoate, and p-hydroxy-m-methoxy-monobenzoate of hydroxymatairesinol; and tetraacetate and tetrabenzoate of secoisolariciresinol. These known compounds are excluded by a disclaimer from the coverage of the novel esters. However, these esters have not been suggested as active ingredients in pharmaceuticals, nutraceutical supplements or any food products. Enterodiol tetraacetate and tetrapropionate are disclosed to possess certain pharmacological properties, EP 43150 A1.

The phenolic esters or diesters of lignans to be administered to the individual shall in this text be understood to cover any geometric isomer or stereoisomer or any mixture of isomers, such as racemates, of these compounds.

The phenolic esters or diesters of lignans to be used in this invention can be supplied in the form of a pharmaceutical preparation, dietary supplement, or a food product.

The pharmaceutical preparation according to this invention is preferably an oral formulation. The required amount of the active compound or mixture of compounds will vary with the compound and the particular condition to be prevented. A typical dose ranges from about 10 to about 2000 mg (calculated as lignan) per day and adult person, preferably 100 to 600 mg per day and adult person. Typical dosage forms include, but are not limited to, oral dosage forms such as powders, granules, capsules, tablets, caplets, lozenges, liquids, elixirs, emulsions and suspensions. All such dosage forms may include conventional carriers, diluents, excipients, binders and additives known to those skilled in the medicinal and pharmaceutical arts.

The carriers typically employed for the pharmaceutical composition or dietary supplement composition may be solid or liquid. Thus, for example, solid carriers include polysaccarides such as lactose, sucrose, gelatin, agar, while liquid carriers include aqueous solutions of salts, polysaccharides, complexing agents, surfactants, syrups, vegetable oils such as peanut oil or olive oil, and certain alcohols. However, any acceptable solid or liquid carrier can be used in the pharmaceutical preparation or other dietary or nutrition formula to be administered according to this invention.

A typical food product, suitable for use in the methods according to this invention, is especially a functional food, a nutritional supplement, a nutrient, a pharmafood, a nutraceutical, a clinical nutritional product, a health food, a designer food or any food product. The term food product shall also be understood to cover groceries and foodstuffs such as flour, other ingredients, certain liquids etc. A suitable concentration of the active compound in the food product is, for example, 1 to 1000 mg of active compound per 100 g of food product, preferably about 10 to 100 mg of active compound per 100 g of food product.

The novel esters according to this invention can be prepared according to the normal routes for esterification, for example by reacting an acid, an acyl halide or anhydride with the lignan in an appropriate solvent.

The invention will be illuminated by the following non-restrictive Experimental Section.

EXPERIMENTAL SECTION

Example 1

Matairesinol Diacetate

Matairesinol (0.5 g, 1.33 mmol) was dissolved into dichloromethane (5 ml). Pyridine (0.25 g, 3.15 mmol) was added and then acetyl chloride (0.23 g, 2.9 mmol) was added dropwise to the mixture. The solution was stirred for three hours at ambient temperature. Then the reaction mixture was washed twice with water (2×5 ml), dried with sodium sulphate, evaporated to dryness and purified by flash chromatography with dichloromethane-ethanol (9.5:0.5) as an eluent. Yield 0.26 g.

$^1$H NMR (200 MHz, CDCl$_3$): 2.29 (s, 3H), 2.31 (s, 3H), 2.56-2.70 (m, 1H), 2.84-3.14 (m, 3H), 3.77 (s, 3H), 3.80 (s, 3H), 3.96 (d, 2H), 4.66 (m, 1H), 6.56-7.05 (m, 6H).

MS (TOF): m/e 481 (M+Na).

EXAMPLE 2

Hydroxymatairesinol Dibutyrate

The compound was prepared according to the method of Example 1 except that hydroxymatairesinol was used as lignan and butyric acid chloride instead of acetyl chloride.

$^1$H NMR (200 M Hz, CDCl$_3$): 1.04 (t, 6H), 1.78 (m, 4H), 2.54 (t, 2H), 2.55 (t, 2H), 2.55-2.68 (m, 1H), 2.8-3.15 (m, 3H), 3.74 (s, 3H), 3.77 (s, 3H), 3.95 (d, 2H), 4.61-4.66 (m, 1H), 6.56-7.00 (m, 6H).

MS (TOF): m/e 537 (M+Na).

EXAMPLE 3

Matairesinol Dibutyrate

The compound was prepared according to the method of Example 1 except that butyric acid chloride instead of acetyl chloride.

$^1$H NMR (200 MHz, CDCl$_3$): 1.05 (t, 6H), 1.79 (m, 4H), 2.55 (t, 4H), 2.45-2.75 (m, 4H), 2.99 (d, 2H), 3.75 (s, 3H), 3.77 (s, 3H), 3.80-3.93 (dd, 1H), 4.10-4.22 (dd, 1H), 6.56-6.95 (m, 6H).

The same compound was also prepared by use of butyric anhydride:

Matairesinol (4 g, 11.2 mmol) was dissolved in 60 ml pyridine and 20 ml CH$_2$Cl$_2$. To the solution, stirred at room temperature under an atmosphere of argon, butyric anhydride (9 g, 56.9 mmol) was added dropwise. The mixture was slowly heated to 50° C. and stirred for 20 h. The solvents were then removed under reduced pressure and the residue was chromatographed on a silica column (1% methanolic CHCl$_3$) yielding the product, which was washed with water and diethyl ether to remove residual butyric acid. Yield 2.45 g, 44%.

EXAMPLE 4

Matairesinol Mesylate

Matairesinol (500 mg, 1.4 mmol) was dissolved in 50 ml pyridine. To the solution stirred at room temperature, mesyl chloride (Methanesulfonyl chloride, 642 mg, 5.6 mmol) was added dropwise. The mixture was heated and stirred at 50° C. for 3 h. The solvent was then removed under reduced pressure and the residue extracted with dichloromethane (50 ml) and water (2×25 ml). The organic phase was dried over NaSO$_4$ and the solvent removed. The residue was chromatographed on a silica column using CHCl$_3$:EtOAc (1:1) as eluent. Yield 543 mg, 75.5%, slightly yellow-brown oil, purity>90% (NMR).

HRMS: calculated for C$_{22}$H$_{26}$O$_{10}$S$_2$ M$^+$ 514.09674, found 514.0969.

$^1$H NMR (400 MHz, CDCl$_3$) δ (ppm): 2.45 (m, 1H), 2.55-2.69 (m, 3H), 2.93 (dd, 2H, J=5.7, 1.9 Hz), 3.13 (s, 3H,), 3.78 (s, 3H), 3.79 (s, 3H), 3.86 (t, 1H, J=9.0 Hz), 4.16 (dd, 1H, J=9.0, 7.5 Hz), 6.58 (dd, 1H, J=1.9, 8.2 Hz), 6.58 (d, 1H, J=1.9 Hz), 6.62 (dd, 1H, J=1.9, 8.2 Hz), 6.79 (d, 1H, J=1.9 Hz), 7.12-7.16 (m, 2H).

EXAMPLE 5

Matairesinol Stearate

Matairesinol (500 mg, 1.4 mmol) was dissolved in 25 ml pyridine. To the solution stearic acid anhydride (3.1 g, 5.6 mmol) was added in small portions. The temperature was raised to 65° C. and the mixture was stirred for 24 h. The solvent was removed under reduced pressure and the residue dissolved in dichloromethane. Unreacted stearic anhydride and stearic acid precipitated from the dichloromethane solution and were filtered off. The solvent was then removed and the residue was washed with n-hexane to afford matairesinol stearate as a white solid. Yield 514 mg, 41%. Purity approximately 90%, consisting of some free stearic acid and acid anhydride (NMR).

LC/MS-ion trap, EIMS: m/z (908.7 M+NH$_4^+$), (890 M$^+$).

$^1$H NMR (400 MHz, CDCl$_3$) δ (ppm): 0.86(t, 6H, J=7.1 Hz), 1.25 (m, 60H), 1.74 (m, 4H), 2.45-2.69 (m, 8H), 2.96 (d, 2H, J=5.9 Hz), 3.73 (s, 3H), 3.75 (s, 3H) 3.86 (dd, 1H, J=9.2, 8.0 Hz), 4.15 (dd, 1H, J=9.2, 7.3 Hz), 6.54 (d, 1H, J=1.8 Hz), 6.56 (dd, 1H, J=1.8, 8.0 Hz), 6.63 (dd, 1H, J=1.8, 8.1 Hz), 6.75 (d, 1H, J=1.8 Hz), 6.90 (d, 1H, J=8.0 Hz), 6.91 (d, 1H, J=8.1 Hz).

EXAMPLE 6

Matairesinol Succinate

Matairesinol (500 mg, 1.4 mmol) was dissolved in 30 ml pyridine. To the solution succinic anhydride (700 mg, 7 mmol) was added in small portions. The temperature was adjusted to 50° C. and the mixture was stirred for 24 h. The solvent was removed under reduced-pressure and the residue dissolved in dichloromethane and extracted first with slightly basic water. The water phase was then acidified with 10% HCl and extracted with dichloromethane. The organic phases were combined, concentrated and chromatographed on a silica column using CHCl$_3$:EtOAc (1:1) as eluent. The fractions containing the product were combined and the solvents were removed.

Analyses by NMR spectroscopy showed a mixture of products (matairesinol and matairesinol succinate) in approximately equal amounts. Likewise, TLC analyses showed two spots and indicated a change in the composition of the product. A parallel reaction performed at almost equal conditions yielded exactly the same results.

EXAMPLE 7

Matairesinol Methylsuccinate

Monomethyl succinate (1 g, 7.56 mmol) was stirred in a flame dried round bottomed flask. Thionyl chloride was added (30 ml, 4.5 g) dropwise and the mixture was heated to 60° C. for 3 h. Then, excess thionyl chloride was removed under reduced pressure and the residue was analysed by NMR spectroscopy. The fully chlorinated product was dissolved in 20 ml dry $CH_2Cl_2$ and dropwise added to a solution of matairesinol (1 g) in 40 ml $CH_2Cl_2$ and 1.8 g pyridine (8 eqv.) at 0° C. The mixture was stirred and allowed to warm to room temp over night. The mixture was then extracted with 2×50 ml water and the organic phase was dried and concentrated. The residue was chromatographed on a silica column (eluent EtOAc:PE 1:1) to yield a fraction containing the product. Yield 1.1 g (purity 80%, NMR, some other components present). The product was rechromatographed with $CHCl_3$ to yield 0.92 g (70%) of a pure fraction containing two components, totally coeluting. The mixture was analysed with LC-MS (ESI-ion trap) and the components were identified as free matairesinol and matairesinol bis methylsuccinate (product). According to NMR analyses the product contained approximately 15% free matairesinol. It seems unlikely that the components can be separated by normal column chromatography. However, pure product can probably be obtained by varying the ratio of reagents (excess of acid chloride).

$^1$H NMR (400 MHz, $CDCl_3$, 30° C.) δ (ppm): 2.4-2.7 (m, 4H), 2.73 (t, 4H, J=7 Hz), 2.89 (t, 4H, J=7 Hz), 2.95 (d, 2H, J=5.9), 3.69 (s, 6H), 3.72 (s, 3H), 3.73 (s, 3H), 3.86 (dd, 1H, J=9.2, 8.1 Hz), 4.14 (dd, 1H, J=7.4, 9.2 Hz), 6.53 (d, 1H, J=1.9 Hz), 6.56 (dd, 1H, J=1.9, 8.0 Hz), 6.62 (dd, 1H, J=1.9, 8.0 Hz), 6.74 (d, 1H, J=1.9 Hz), 6.91 (d, 1H, J=8.0 Hz), 6.93 (d, 1H, J=8.0 Hz).

EXAMPLE 8

Secoisolariciresinol Tetrabutyrate

Secoisolariciresinol (270 mg, 0.745 mmol) was dissolved in 30 ml pyridine. To the stirred solution butyric acid chloride (630 mg, 5.95 mmol) was added dropwise. The mixture was stirred and heated to 50° C. and then the heating was switched off and the mixture was allowed to cool to room temperature over night. The solvent was removed under reduced pressure and the residue extracted with dichloromethane-water. The organic phase was dried over $NaSO_4$ and the solvent removed. The residue was redissolved in diethyl ether, which yielded a precipitate upon standing. The precipitate was filtered off (did not contain the product) and the solution was chromatographed on a silica column using $CHCl_3$:MeOH 99:1 as eluent yielding 330 mg of a yellow oil (yield 69%). NMR analysis showed some extra signals at the aromatic region, possibly pyridinium impurities. When the product was washed in water-chloroform the signals of the impurities were reduced, but they still remained in the product. The product was then rechromatographed with EtOAc:petrol ether (1:1) to yield a very pure fraction (colourless oil).

$^1$H NMR (250 MHz, $CDCl_3$) δ (ppm): 0.95 (t, 6H, J=7.5 Hz), 1.05 (t, 6H, J=7.5 Hz), 1.65 (m, 4H, J=7.5 Hz), 1.79 (m, 4H, J=7.5 Hz), 2.10 (m, 2H), 2.29 (t, 4H, J=7.5 Hz), 2.54 (t, 4H, J=7.5 Hz), 2.67 (m, 4H), 3.73 (s, 6H), 4.00 (dd, 2H, J=5.8, 11.3 Hz), 4.25 (dd, 2H, J=5.5, 11.3 Hz), 6.60 (complex, 4H), 6.89 (d, 2H, J=7.7).

EXAMPLE 9

Enterolactone Butyrate

Enterolactone (154 mg) was dissolved in 10 ml pyridine and 10 ml $CH_2Cl_2$ (flame dried glassware) The mixture was stirred under Ar and butyric anhydride (4 ekv., 328 mg) was dropwise added at room temperature. The temperature was raised to 50° C. and the mixture was allowed to react for 5 h. Then toluene was added and the solvents were removed under reduced pressure (azeotropic distillation of pyridine with toluene using a rotary evaporator). The residue was then extracted in water:$CH_2Cl_2$, the organic phase was dried and the solvent removed under reduced pressure to yield a colourless oil. The product was analysed by GC-MS, (purity ~97%). However, NMR spectroscopic analyses revealed that much butyric acid and anhydride was left in the sample. The residue was then chromatographed on a silica column with chloroform to yield a colourless oil (purity by GC/MS 97%). Analyses by NMR spectroscopy showed a pure enterolactone butyrate fraction, but the butyric acid was not completely removed. Integration of the free butyric acid signals and those of the esterified, gave the ratio 85:15 (1H NMR, 500 MHz). However, when the product was dried under vacuum most of the free butyric acid was removed to yield 160 mg (71%) enterolactone-butyrate (1H NMR 250 MHz).

EIMS: m/z 438 (2, M$^+$), 368 (100), 298 (47), 191 (22), 133 (10), 108 (89), 71 (75).

$^1$H NMR (500 MHz, $CDCl_3$) δ (ppm): 1.05 (t, 6H, J=7.4 Hz), 1.79 (m, 4H, J=7.4 Hz), 2.51-2.71 (m, 8H), 2.96 (dd, 1H, J=7.0, 14.1 Hz), 3.07 (dd, 1H, J=5.3, 14.1 Hz), 3.85 (dd, 1H, J=5.8, 9.3 Hz), 4.12 (dd, 1H, J=5.4, 9.3 Hz), 6.78 (t, 1H, J=1.8 Hz), 6.88 (d, 1H, J=7.6 Hz), 6.91 (t, 1H, J=1.8 Hz) 6.93-6.98 (2dd, 2H), 7.02 (d, 1H, J=7.6 Hz), 7.26 (t, 1H, J=7.6 Hz), 7.29 (t, 1H, J=7.6 Hz).

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

Scheme 1

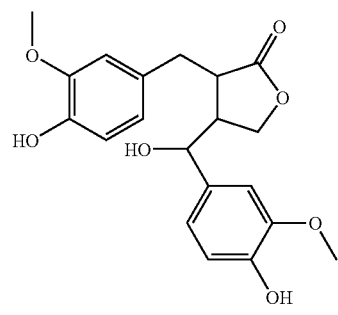

Hydroxymatairesinol

-continued
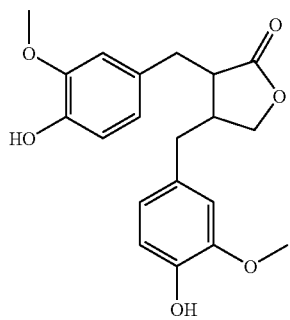
Matairesinol
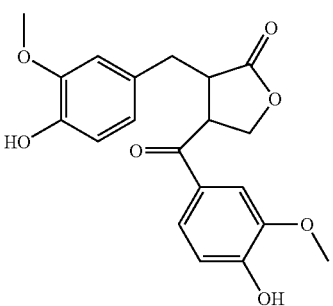
Oxomatairesinol
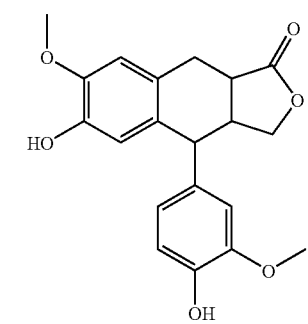
Conidendrin
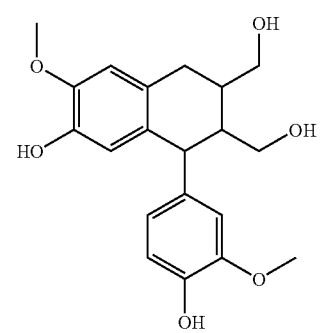
Isolariciresinol
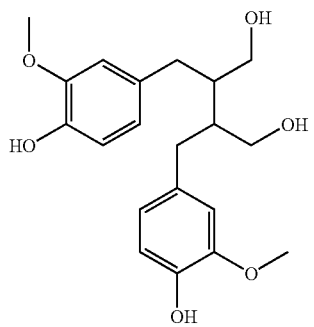
Secoisolariciresinol
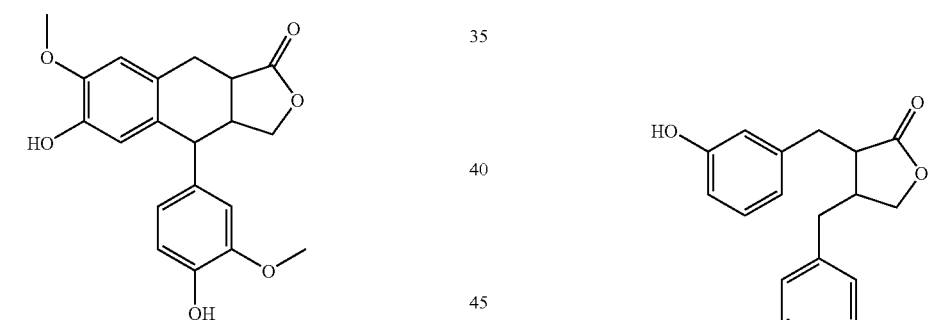
Nortrachelogenin
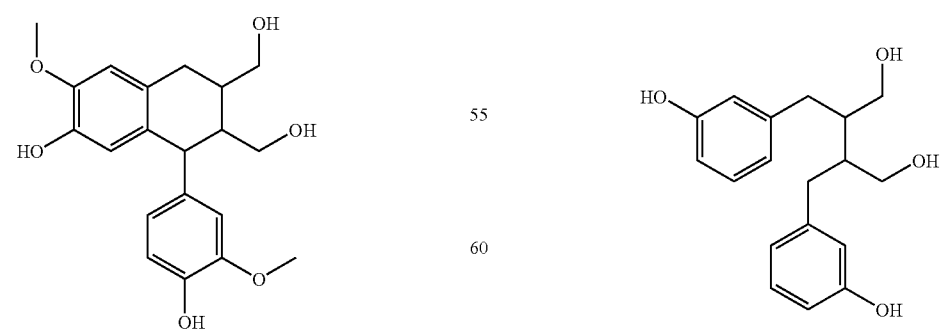
Enterolactone
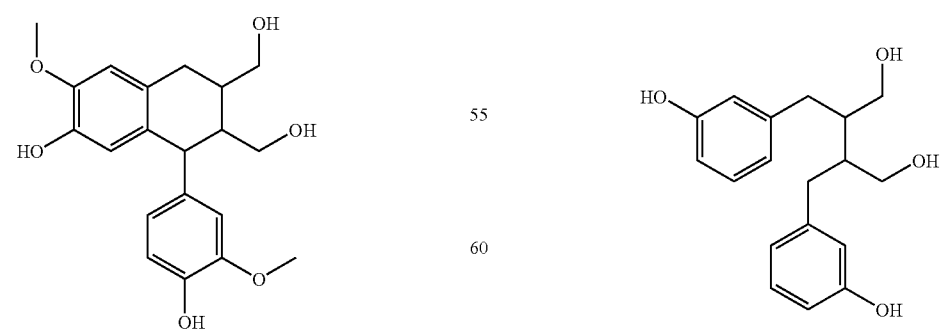
Enterodiol

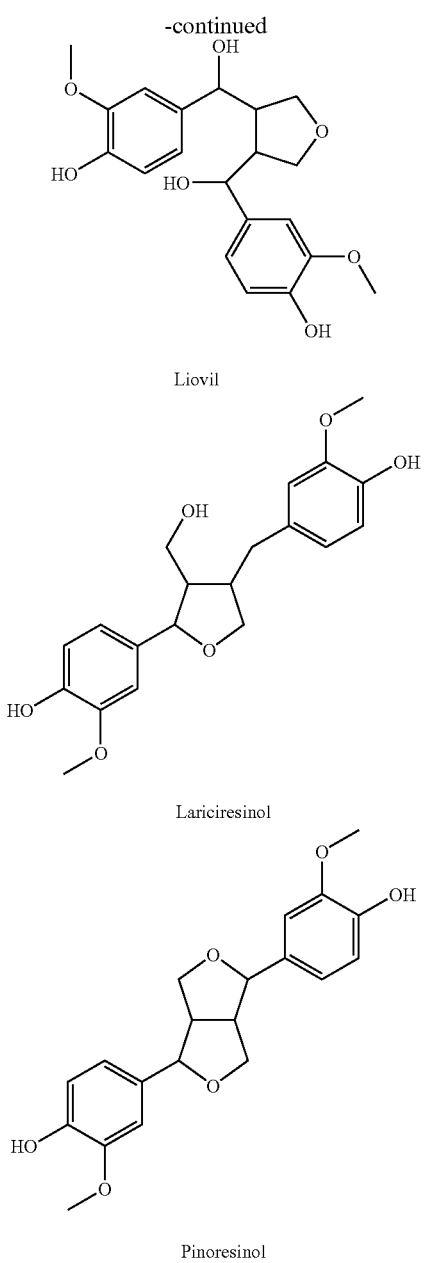

Liovil

Lariciresinol

Pinoresinol

REFERENCES

Ekman R: Distribution of lignans in Norway spruce. Acta Academiae Aboensis, Ser B, 39:1-6, 1979.

Axelson M, Sjövall J, Gustafsson B E and Setchell K D R: Origin of lignans in mammals and identification of a precursor from plants. Nature, 298: 659-660, 1982.

Heinonen S, Nurmi T, Liukkonen K, Poutanen K, Wahala K, Deyama T, Nishibe S, Adlercreutz H (2001) In vitro metabolism of plant lignans: new precursors of mammalian lignans enterolactone and enterodiol. J Agric Food Chem, 49, 3178-86.

Adlercreutz (1998) Phytoestrogens and human health, In: Reproductive and Developmental Toxicology (edited by Korach, K.). pp. 299-371, Marcel & Dekker, NY.

Vanharanta M, Voutilainen S, Nurmi T, Kaikkonen J, Roberts L J, Morrow J D, Adlercrutz H, Salonen J T (2002). Association between low serum enterolactone and increased plasma F(2)-isoprostanes, a measure of lipid peroxidation. Atherosclerosis 60, 465.

Avivi-Green C., Polak-Charcon S., Madar Z. and Schwartz B. (2000) Apoptosis cascade proteins are regulated in vivo by high intracolonic butyrate concentration: correlation with colon cancer inhibition. Oncol. Res. 12, 83-95.

Gostner A., Dusel G., Kelber E., Scheppach W. and Bartram H. P. (2000) Comparisons of the anti-proliferative effects of butyrate and aspirin on human colonic mucosa in vitro. Eur. J. Cancer Prev. 9, 205-11.

Belobrajdic D. P. and McIntosh G. H. (2000) Dietary butyrate inhibits NMU-induced mammary cancer in rats. Nutr. Cancer 36, 217-233.

Bordonaro M., Mariadason J. M., et al., (1999) Butyrate-induced apoptotic cascade in colonic carcinoma cells: modulation of the beta-catenin-Tcf pathway and concordance with effects of sulindac and trichostatin A but not curcumin. Cell Growth Differentiation 10, 713-720

Chang J-G., Hsieh-Li H-M., et al. (2001) Treatment of spinal muscular atrophy by sodium butyrate. PNAS 98, 9808-9813

Han Z., Cao Z., Chatterjee D., Wyche J. and Pantazis P. (1999) Propionate and butyrate esters of camptothecin and 9-nitrocamptothecin as antileukemia prodrugs in vitro. Eur. J. Haematol. 62, 246-55

Heerdt B. G., Houston M. A., et al. (1999) Initiation of growth arrest and apoptosis of MCF-7 mammary carcinoma cells by tributyrin, a triglyceride analogue of the short chain fatty acid butyrate, is associated with mitochondrial activity. Cancer Res. 59, 1584-1591

McBain J. A., Eastman A., et al (1997) Apoptotic death in ednocarinoma cell lines induced by butyrate and other histone deacetylase inhibitors. Biochem. Pharmacol. 53, 1357-1368.

Nudelman A and Raphaeli A (2000) Novel mutual prodrug of retinoic and butyric acids with enhanced anticancer activity. J. Med. Chem. 43, 2962-2966.

Säeman M. D., Böhmig G. A., et al., (2000) Anti-inflammatory effects of sodium butyrate on human monocytes: potent inhibition of IL-12 and up-regulation of IL-10 production. FASEB J. 14, 2380-2382

The invention claimed is:
1. Hydroxymatairesinol dibutyrate.
2. A pharmaceutical composition or dietary supplement composition comprising an active ingredient and an acceptable carrier, wherein said active ingredient is hydroxymatairesinol dibutyrate.

* * * * *